US007414106B2

(12) United States Patent
Camarero et al.

(10) Patent No.: US 7,414,106 B2
(45) Date of Patent: Aug. 19, 2008

(54) SYNTHESIS OF PEPTIDE α-THIOESTERS

(75) Inventors: Julio A. Camarero, Livermore, CA (US); Alexander R. Mitchell, Livermore, CA (US); James J. De Yoreo, Clayton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 685 days.

(21) Appl. No.: 10/871,346

(22) Filed: Jun. 18, 2004

(65) Prior Publication Data

US 2007/0129537 A1 Jun. 7, 2007

Related U.S. Application Data

(60) Provisional application No. 60/480,077, filed on Jun. 19, 2003.

(51) Int. Cl.
*C07K 1/00* (2006.01)
*C07K 1/02* (2006.01)
*C07K 1/06* (2006.01)
*C07K 1/14* (2006.01)

(52) U.S. Cl. ...................... 530/333; 530/334; 530/335; 530/337; 530/344

(58) Field of Classification Search ...................... None
See application file for complete search history.

(56) References Cited

OTHER PUBLICATIONS

Ludolph B, Eisele F, Waldmann, H, SOlid-Phase Synthesis of Lipidated Peptide, Journal of American Chemical Society Communications, 2002, 124: 5954-5955.*

Carmarero JA, Muir TW, Biosynthesis of a Head-to-Tail Cyclized Protin with Improved Biological Activity, Journal of American Chemical Society Communications, 1999, 121: 5597-5598.*

Murray Goodmand, Kenneth C. Stueben, Peptide Syntheses Via Amino Acid Active Esters, *J.Am. Chem. Soc.* 1959, 81, 3980.

* cited by examiner

*Primary Examiner*—Anish Gupta
*Assistant Examiner*—Julie Ha
(74) *Attorney, Agent, or Firm*—John H. Lee; Ann M. Lee

(57) ABSTRACT

Disclosed herein is a new method for the solid phase peptide synthesis (SPPS) of C-terminal peptide α thioesters using Fmoc/t-Bu chemistry. This method is based on the use of an aryl hydrazine linker, which is totally stable to conditions required for Fmoc-SPPS. When the peptide synthesis has been completed, activation of the linker is achieved by mild oxidation. The oxidation step converts the acyl-hydrazine group into a highly reactive acyl-diazene intermediate which reacts with an α-amino acid alkylthioester (H-AA-SR) to yield the corresponding peptide α-thioester in good yield. A variety of peptide thioesters, cyclic peptides and a fully functional Src homology 3 (SH3) protein domain have been successfully prepared.

16 Claims, 7 Drawing Sheets

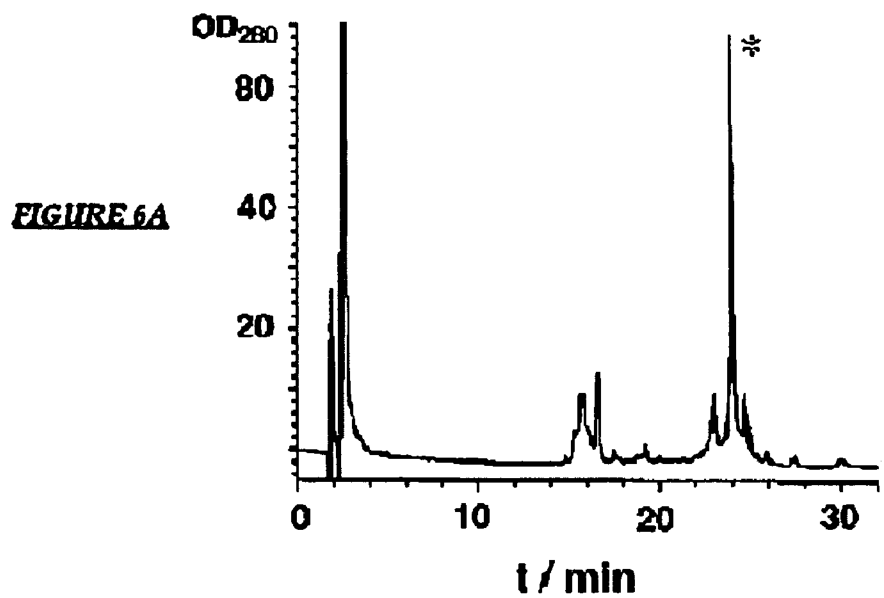
FIGURE 6A
ESMS
+4
+5
+7
+6
+3
m/ z
FIGURE 6B
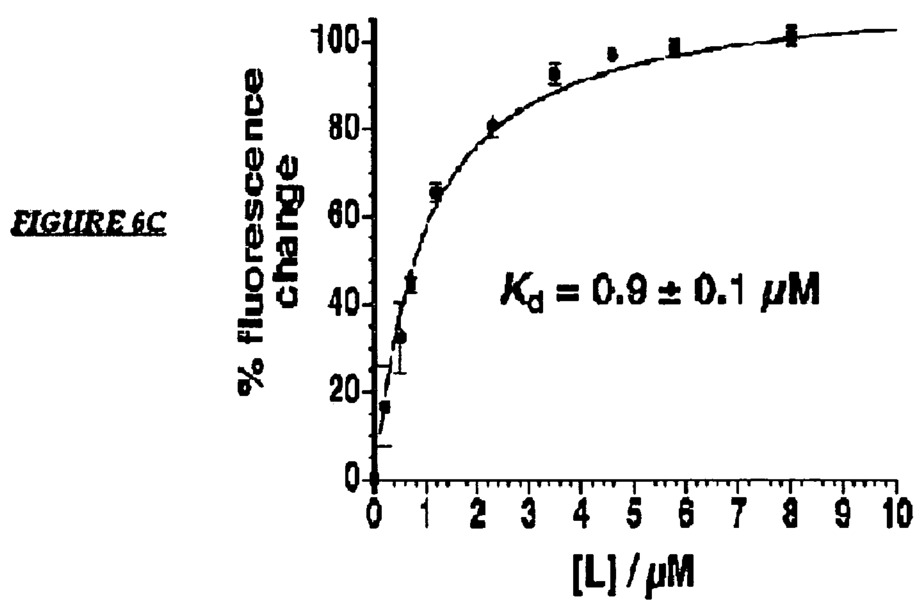
FIGURE 6C

SYNTHESIS OF PEPTIDE α-THIOESTERS

RELATED APPLICATION

This application claims the benefit of U.S. Provisional Application No. 60/480,077 filed Jun. 9, 2003 entitled, "Synthesis of Peptide α-Thioesters" which is incorporated herein by this reference.

The following is a listing of data files contained on a duplicate set of replacement compact disks. The material contained on the compact disk is incorporated by reference herein.

COPY 1 REPLACEMENT Mar. 24, 2005

File Name: 11175S.APP.: File size: 2.81 KB; File creation date: Mar. 24, 2005

COPY 2 REPLACEMENT Mar. 31, 2005

File Name: 11175S.APP.: File size: 2.81 KB; File creation date: Mar. 31, 2005

The United States Government has rights in this invention pursuant to Contract No. W-7405-ENG-48 between the United States Department of Energy and The University of California for the operation of Lawrence Livermore National Laboratory.

BACKGROUND

C-terminal peptide α-thioesters are key intermediates in the synthesis of small and medium-sized proteins and cyclic peptides by native chemical ligation. These mildly activated species are also required for the construction of topologically and backbone engineered proteins.

C-terminal peptide α-thioesters can be prepared by standard solid-phase peptide synthesis (SPPS) using Boc/benzyl chemistry, or for larger polypeptide domains and protein domains, using intein-based bacterial expression systems. The Boc/benzyl approach requires the use of anhydrous HF which is not well suited for synthesis of phospho- and glyco-peptides. In addition, anhydrous HF is very toxic and requires special equipment for handling.

The Fmoc-based methodology is attractive as it does not employ HF and hence provides the synthesis of phospho- and glyco-peptides in good yields. However, the poor stability of the thioester functionality to strong nucleophiles such as piperidine, which is used for the deprotection of the $N^{\alpha}$-Fmoc group, seriously limits the use of this methodology for the preparation of peptide α-thioesters. So far, several approaches have been used to overcome this limitation. Futaki et al. used an approach where peptide α-thioesters were prepared in solution using a partially protected precursor. (See Futaki, S.; Sogawa, K.; Maruyama, J.; Asahara, T.; Niwa, M. *Tetrahedron Lett.* 1997, 38, 6237.) Li et al. used a Fmoc-deprotection cocktail compatible with α-thioesters to synthesize an unprotected 25-residue peptide α-thioester in moderate yield. (See Li, X. Q.; Kawakmi, T.; Aimoto, S. *Tetrahedron Lett.* 1998, 39, 8669.) A similar approach was also used by Clippingdale et al. using in this case a non-nucleophilic base in combination with 1-hydroxybenzotriazole (HOBt). (See Clippingdale, A. B.; Barrow, C. J.; Wade, J. D. *J. Pept. Sci.* 2000, 6, 225.)

Alternatively, the introduction of the α-thioester function at the end of a synthesis has been used by Alsina et al. where the backbone amide linker (BAL) was employed for the synthesis of peptide thioesters using an Fmoc-based strategy. This approach was used for the synthesis of small peptide thioesters in good yields. However, some racemization was observed during the thiolysis step. Swinnen et al used the phenylacetamidomethyl (PAM) and Wang resins to synthesize peptide α-thioesters by employing EtSH in the presence of $Me_2AlCl$ to effect thiolysis of the resin-bound peptide. This approach was used for the synthesis of a 22-residue peptide α-thioester in moderate yield. Another approach developed by Ingenito et al. and Shin et al. involved the use of Kenner's sulfonamide safety-catch linker. This linker is fully stable to repetitive exposure to the basic conditions needed for Fmoc deprotection. When the sulfonamide is alkylated, the peptide resin is activated and easily cleaved with thiols to yield the corresponding peptide α-thioester. However, the use of akylating agents (such as $CH_2N_2$ or $ICH_2CN$) has been shown to alkylate unprotected methionine residues. More recently, Brask et al. have introduced a new method for the generation of peptide thioesters using a trithioortho ester linker. (See Brask, J.; Albericio, F.; Jensen, K. J. *Org. Lett.* 2003, 5, 2951.)

REFERENCES

Dawson, P. E.; Kent, S. B. *Annu. Rev. Biochem.* 2000, 69, 923.

Tam, J. P.; Xu, J. X.; Eom, K. D. *Biopolymers* 2001, 60, 194.

Muir, T. W. *Annu. Rev. Biochem.* 2003, 72, 249.

Camarero, J. A.; Muir, T. W. *J. Chem. Soc., Chem. Comm.* 1997, 1997, 1369.

Zhang, L.; Tam, J. P. *J. Am. Chem. Soc.* 1997, 119, 2363.

Camarero, J. A.; Cotton, G. J.; Adeva, A.; Muir, T. W. *J. Pept. Res.* 1998, 51, 303.

Shao, Y.; Lu, W. Y.; Kent, S. B. H. *Tetrahedron Lett.* 1998, 39, 3911.

Tam, J. P.; Lu, Y. A.; Liu, C. F.; Shao, J. *Proc Natl Acad Sci* USA 1995, 92, 12485.

Camarero, J. A.; Pavel, J.; Muir, T. W. *Angew. Chem. Int. Ed.* 1998, 37, 347.

Camarero, J. A.; Muir, T. W. *J. Am. Chem. Soc.* 1999, 121, 5597.

Iwai, H.; Pluckthum, A. *FEBS Lett.* 1999, 166.

Yu, Q. T.; Lehrer, R. I.; Tam, J. P. *J. Biol. Chem.* 2000, 275, 3943.

Camarero, J. A.; Fushman, D.; Sato, S.; Giriat, I.; Cowburn, D.; Raleigh, D. P.; Muir, T. W. *J Mol Biol* 2001, 308, 1045.

Lu, W.; Qasim, M. A.; Laskowski, M.; Kent, S. B. H. *Biochemistry* 1997, 36, 673.

Lu, W. Y.; Randal, M.; Kossiakoff, A.; Kent, S. B. H. *Chem. Biol.* 1999, 6, 419.

Baca, M.; Kent, S. B. H. *Tetrahedron* 2000, 56, 9503.

Hojo, H.; Aimoto, S. *Bull. Chem. Soc. Jpn.* 1991, 64, 111.

Hackeng, T. M.; Griffin, J. H.; Dawson, P. E. *Proc. Natl. Acad. Sci.* USA 1999, 96, 10063.

Camarero, J. A.; Adeva, A.; Muir, T. W. *Lett. Pept. Sci.* 2000, 7, 17.

Camarero, J. A.; Muir, T. W. *Current Protocols in Protein Science* 1999, 1-21.

Perler, F. B.; Adam, E. *Curr. Opin. Biotechnol.* 2000, 377.

Muir, T. W.; Sondhi, D.; Cole, P. A. *Proc. Natl. Acad. Sci. USA* 1998, 95, 6705.

Huse, M.; Holford, M. N.; Kuriyan, J.; Muir, T. W. *J. Am. Chem. Soc.* 2000, 122, 8337.

Shin, Y.; Winans, K. A.; Backes, B. J.; Kent, S. B. H.; Ellman, J. A.; Bertozzi, C. R. *J. Am. Chem. Soc.* 1999, 121, 11684.

Tolbert, T. J.; Wong, C.-H. *J. Am. Chem. Soc.* 2000, 122, 5421.

Miller, J. S.; Dudkin, V. Y.; Lyon, G. J.; Muir, T. W.; Danishefsky, S. J. *Angew. Chem. Int. Ed.* 2003, 42, 431.

Alsina, J.; Yokum, T. S.; Albericio, F.; Barany, G. *J. Org. Chem.* 1999, 64, 8671.

Swinnen, D.; Hilvert, D. *Org. Lett.* 2000, 2, 2439.

Mitchell, A. R.; Erickson, B. W.; Ryabtsev, M. N.; Hodges, R. S.; Merrifield, R. B. *J. Am. Chem. Soc.* 1976, 98, 7357.

Wang, S.-S. *J. Am. Chem. Soc.* 1973, 95, 1328.

Sewing, A.; Hilvert, D. *Angew. Chem. Int. Ed.* 2001, 40, 3395.

Ingenito, R.; Bianchi, E.; Fattori, D.; Pessi, A. *J. Am. Chem. Soc.* 1999, 121, 11369.

Kenner, G. W.; McDermott, J. R.; Sheppard, R. C. *Chem. Comm.* 1971, 636.

Flavell, R. R.; Huse, M.; Goger, M.; Trester-Zerdlitz, M.; Kuriyan, J.; Muir, T. W. *Org. Lett.* 2002, 4, 165.

SUMMARY OF THE INVENTION

An aspect of the invention includes a method comprising: providing a solid phase peptide having a hydrazide linker; oxidizing said hydrazide linker to form a solid phase peptide having an acyl diazene derivative; and cleaving said acyl diazene derivative with an S-nucleophile.

Another aspect of the invention includes a method comprising: providing a solid phase peptide having a hydrazine linker; oxidizing said hydrazide linker to form a solid phase peptide having an acyl diazene derivative; and cleaving said acyl diazene derivative with a thiol.

A further aspect of the invention includes a method comprising: providing a protected solid phase peptide having a hydrazide linker; oxidizing said hydrazide linker to form a solid phase peptide having an acyl diazene derivative; and cleaving said acyl diacene derivative with an alpha amino thioester.

BRIEF DESCRIPTION OF THE DRAWINGS

FIG. 6A is an HPLC analysis of the intermolecular ligation reaction between peptide thioester SEQ ID NO:9 and peptide SEQ ID NO: 10 after 36 hours.

FIG. 6B shows an ESMS of ligated SH3 domain.

FIG. 6C shows the change in fluorescence emission intensity of the ligated SH3 domain upon addition of proline-rich peptide ligand SEQ ID NO: 11.

DETAILED DESCRIPTION

Disclosed herein is a new strategy for the synthesis of peptide α-thioesters using an Fmoc-based approach. The method is based on the use of an aryl-hydrazine linker that is totally stable to the conditions of Fmoc- and Boc-SPPS, to yield a peptide hydrazide resin. Mild oxidation of the peptide hydrazide resin affords a peptidyl diazene resin which is used to prepare C-terminal peptide α-thioesters.

REFERENCES

Wolman, Y.; Gallop, P. M.; Patchornik, A. *J. Am. Chem. Soc.* (1961), 83, 1263.

Milne, H. B.; Most, C. F. *J. Org. Chem.* (1968), 33, 169.

Wieland, T.; Leawalter, J.; Birr, C. *Liebigs Ann. Chem.* (1970), 740, 31.

Semenov, A. N.; Gordeev, K. Y. *Int. J. Peptide Protein Res.* (1995), 45, 303.

Millington, C. R.; Quarrell, R.; Lowe, G. *Tetrahedron Lett.* (1998), 39, 7201.

Stieber, F.; Grether, U.; Waldmann, H. *Angew. Chem. Int. Ed.* (1999), 38, 1073.

Berst, F.; Holmes, A. B.; Ladlow, M.; Murray, P. J. *Tetrahedron Lett.* (2000), 41, 6649.

Rosenbaum, C.; Waldmann, H. *Tetrahedron Lett.* (2001), 42, 5677.

Peters, C.; Waldmann, H. *J. Org. Chem.* (2003), 68, 6053.

Ludolph, B.; Waldmann, H. *Chem. Eur. J.* (2003), 9, 3683.

General Synthetic Scheme

Figure 1:
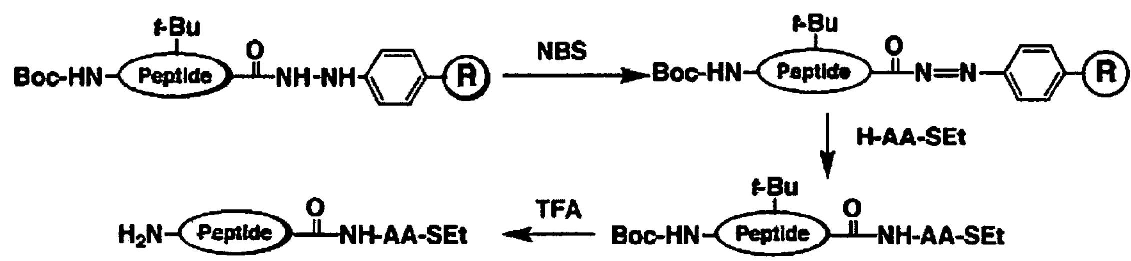
FIG. 1 shows the synthetic scheme for the preparation of C-terminal peptide α-thioesters using Fmoc-based solid phase peptide synthesis on an aryl hydrazine support.

FIG. 1 shows the synthetic scheme for the preparation of peptide α-thioesters using an aryl hydrazine support. The Fmoc-based methodology described herein uses t-Bu based side-chain protection (Fmoc/t-Bu chemistry). In addition, the last amino acid is incorporated as a Boc-derivative to prevent the possible oxidation of the free α-amino group during the oxidation step. A hydrazine safety-catch linker that is totally stable to the conditions used during SPPS by either Boc- or Fmoc-chemistries is employed. The peptide-hydrazine resin is activated by treatment with mild oxidizing agents to provide a reactive acyl diazene intermediate that readily reacts with N- and O-nucleophiles. S-nucleophiles, on the other hand, did not cleave the acycl diazene efficiently. When thiols such as EtSH, BnSH, PhSH or PhS-Na+ were used to cleave the peptidyl diazene resin, only minor amounts (<2%) of the corresponding peptide thioester were detected. A likely explanation for this result could be found in the known redox character of diazene derivatives which could lead to the oxidation of the thiol to the corresponding disulfide (See March, *J. Advanced Organic Chemistry,* Reactions, mechanisms and structure; John Wiley & Sons: NY, 1992, pp. 1205). α-Amino acid S-alkyl thioesters react with a highly reactive peptidyl (acyl) diazene in the presence of the mildly reactive alkyl thioester group. The reaction selectively cleaves the peptide from the diazene resin furnishing the corresponding C-terminal peptide α-thioester.

The procedure outlined in FIG. 1 for C-terminal peptide α-thioester synthesis by Fmoc-chemistry involves the direct assembly of the peptide on a phenyl hydrazine resin using standard Fmoc protocols. (See Atherton, E.; Sheppard, R. C. *Solid phase peptide* synthesis: a practical approach; Oxford University Press: Oxford, 1989). Acylation of hydrazines produces acyl-hydrazines, also known as hydrazides. Oxidation of amino acid or peptide hydrazides provides the corresponding amino acid or peptide diazenes generically known as acyl-diazenes. At the end of the synthesis, the fully protected peptide-resin is activated by mild oxidation with an oxidizing agent such as N-bromosuccinimide (NBS) in the presence of pyridine. The reactive acyl diazene is then cleaved with an α-amino acid S-alkyl thioester. Finally, the fully protected peptide α-thioester is deprotected with TFA, in the presence of the appropriate scavengers (e.g., trisisopropylsilane (TIS) or ethanethiol (EtSH). Note that in the cases where the N-terminal α-amino group should be unprotected in the final peptide α-thioester, the last amino acid should be incorporated as Boc-$^{\alpha}$N-derivative during the synthesis. This prevents the possible oxidation of the free α-amino group during the oxidation step.

Oxidation of the Resin and Cleavage by α-Amino Acid Thioesters

TABLE 1

| Peptide | Sequence | Mw/Da | | Yield/ % | |
|---|---|---|---|---|---|
| SEQ ID NO: 1 | Ac-IAFG-SEt | 492.6[a] | 492.0[b] | 95[c] | 60[d] |
| SEQ ID NO: 2 | Ac-IAFA-SEt | 506.3[a] | 506.0[b] | 94[c] | 65[d] |
| SEQ ID NO: 3 | H-LFAG-SEt | 450.0[a] | 449.7[b] | 95[c] | 70[d] |

[a]theoretical;
[b]actual;
[c]based on HPLC purity;
[d]based on initial resin substitution The cleavage of the activated peptidyl diazene resin by α-amino acid S-alkyl thioesters was determined. Three model peptides were synthesized on hydrazinobenzyl AM resin as shown in Table 1 and the protected peptide-resins were activated by oxidation with 2 equiv. of NBS in the presence of anhydrous pyridine for 10 min. at room temperature. The commercially available 4-Fmoc-hydrazinobenzoyl AM resin from Novabiochem was used in all experiments. When the oxidation reaction was complete the activated peptide-resin was then washed with dichloromethane (DCM) and cleaved with 20 equiv. of H-AA-SEt (where AA was either Gly or Ala). The reactive H-AA-SEt was generated in situ from the corresponding H-AA-SEt.HCl by adding an excess of N,N-diisopropylethylamine (DIEA) during the cleavage step. Although only peptide thioesters containing either a Gly or Ala at the C-terminal positions were used in this study, it should be noted that other amino acid thioesters can also be used with the appropriate side-chain protection (i.e., trifunctional amino acids). Peptide thioesters containing either Ala or Gly residue at the C-terminus are the most commonly employed intermediates in native chemical ligation reactions. (See Hackeng, T. M.; Griffin, J. H.; Dawson, P. *E. Proc. Natl. Acad. Sci.* USA 1999, 96, 10063.) The reaction was quenched with acetic acid and the solvent evaporated.

Figure 2A:
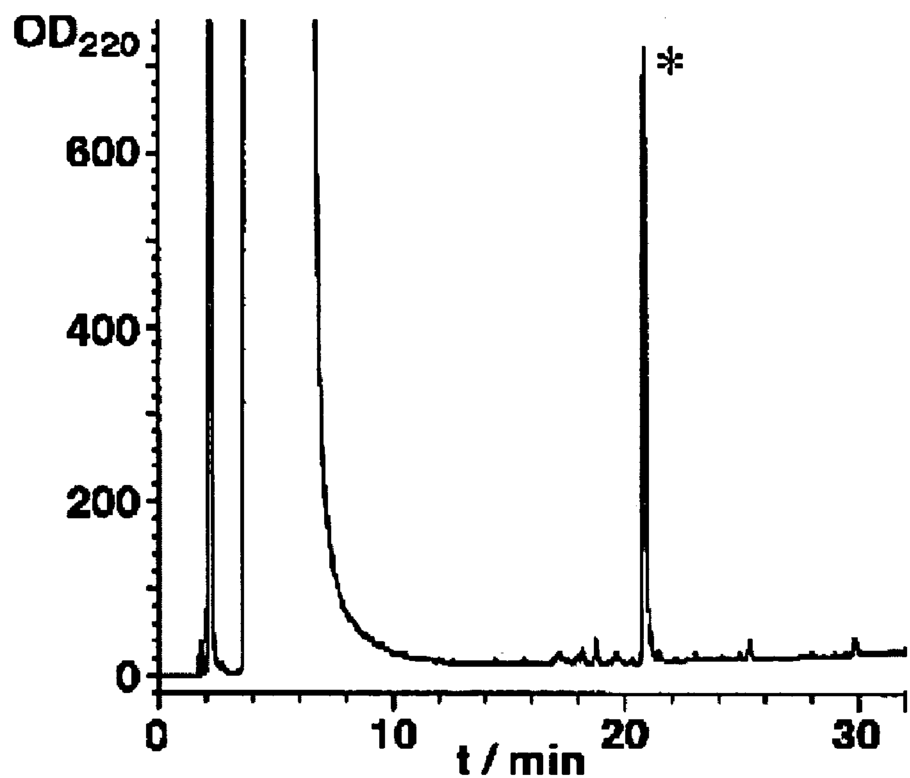
FIGS. 2A-2C show HPLC analysis of peptides SEQ ID NO: 1-SEQ ID NO: 3.
Figure 2B:
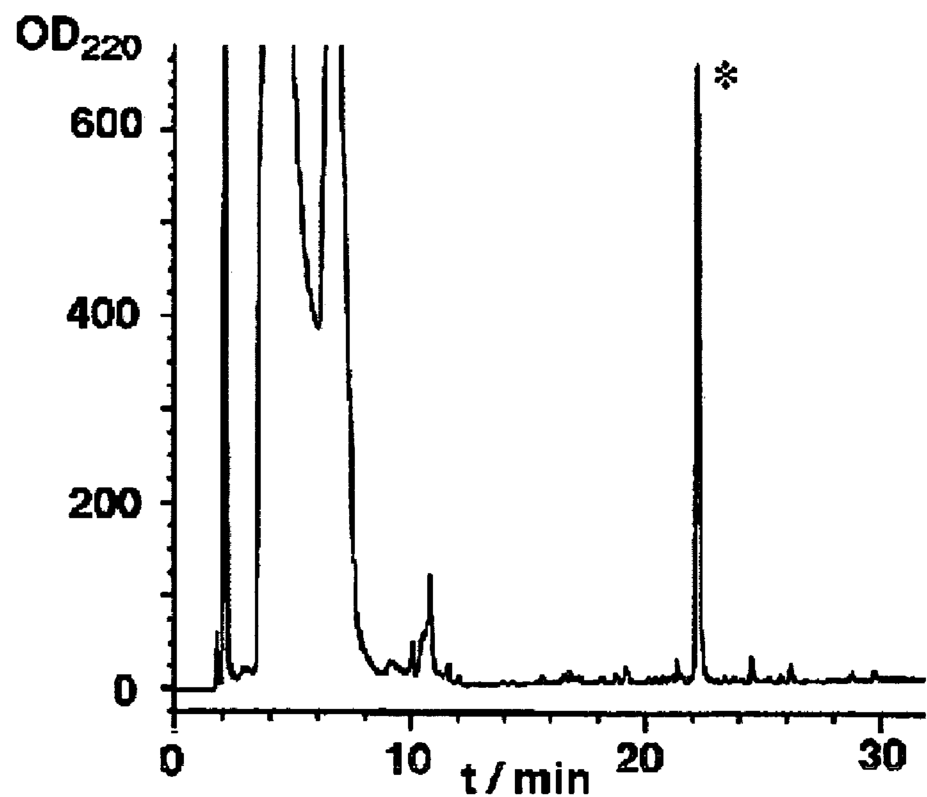
Figure 2C:
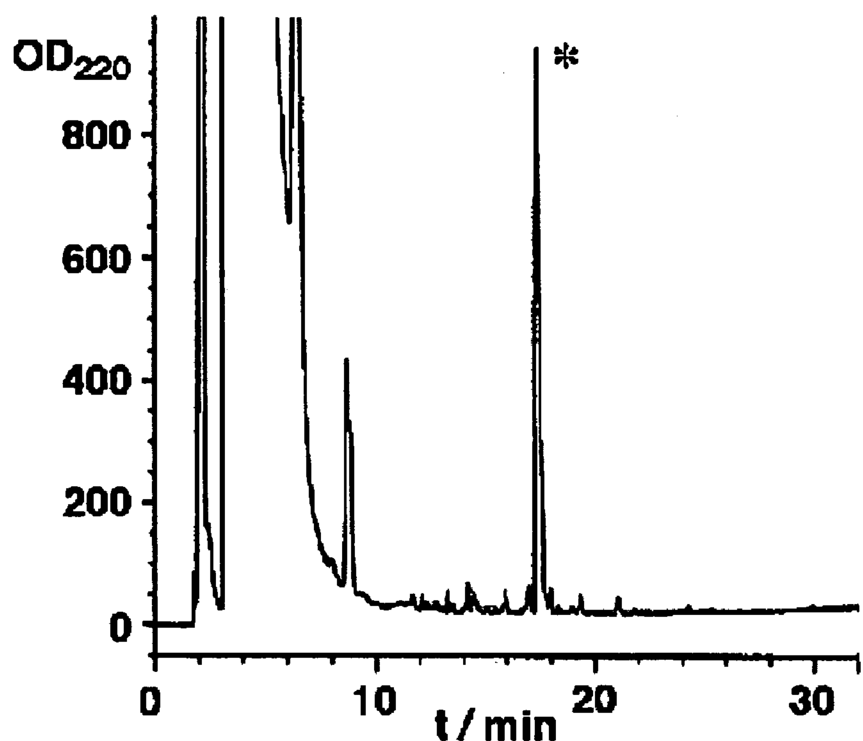
Figure 2D:
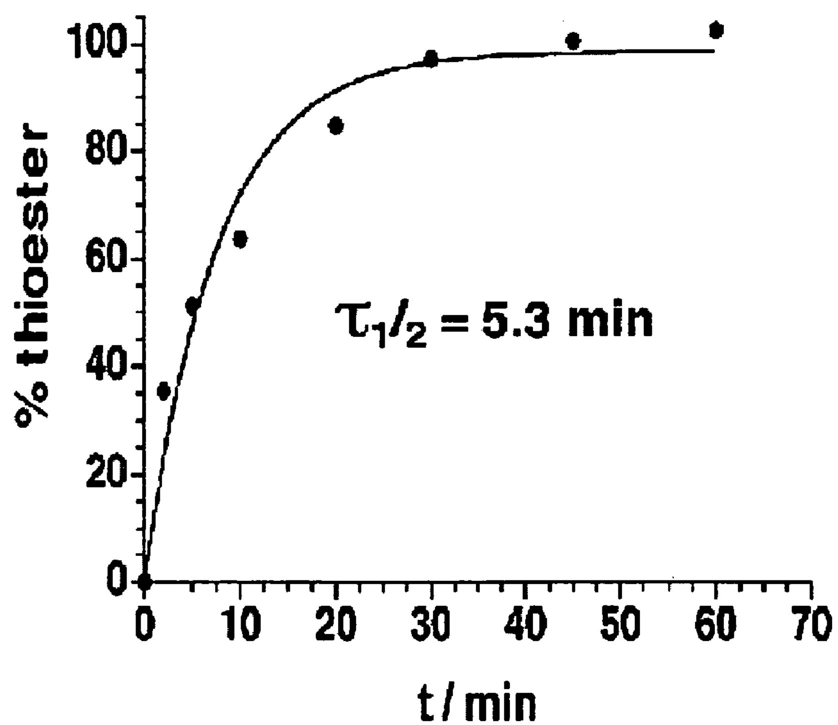
FIG. 2D shows kinetic analysis for the formation of peptide thioester SEQ ID NO: 3.

The peptide α-thioester product was then deprotected with TFA to remove acid-labile protecting groups. The oxidation and cleavage reactions were clean and efficient with all three peptides as shown in Table 1 and FIGS. 2A-2C. FIG. 2A is an HPLC analysis of the crude product obtained by oxidation and cleavage using NBS and H-AA-SEt of peptide SEQ ID NO: 1. FIG. 2B is an HPLC analysis of the crude product obtained by oxidation and cleavage using NBS and H-AA-SEt of peptide SEQ ID NO: 2. FIG. 2C is an HPLC analysis of the crude product obtained by oxidation and cleavage using NBS and H-AA-SEt of peptide SEQ ID NO: 3. In each case the asterisk denotes the peptide thioester product when a linear gradient of 0-70% buffer B (90% $CH_3CN$+9.9% $H_2O$+0.1% TFA) over 30 minutes was used. In each case the main product was the corresponding peptide α-thioester with cleavage yields around 65% and purities around 95% (as calculated by HPLC). Similar cleavage yields were obtained when propylamine was used as a nucleophile to react with the peptidyl diazene resin. Acyl diazene supports are highly reactive toward N-nucleophiles, i.e, the completion of the cleavage reactions occurred in less than 30 minutes. The speed of this reaction minimized the multiple incorporation of amino acid thioester residues at the C-terminus of the peptide during the cleavage step. FIG. 2D is a kinetic analysis for the formation of peptide thioester SEQ ID NO: 3 by oxidation and cleavage with NBS and H-Gly-SEt.

Epimerization of the C-terminal Amino Acid after the Oxidative Cleavage

Figure 3A:
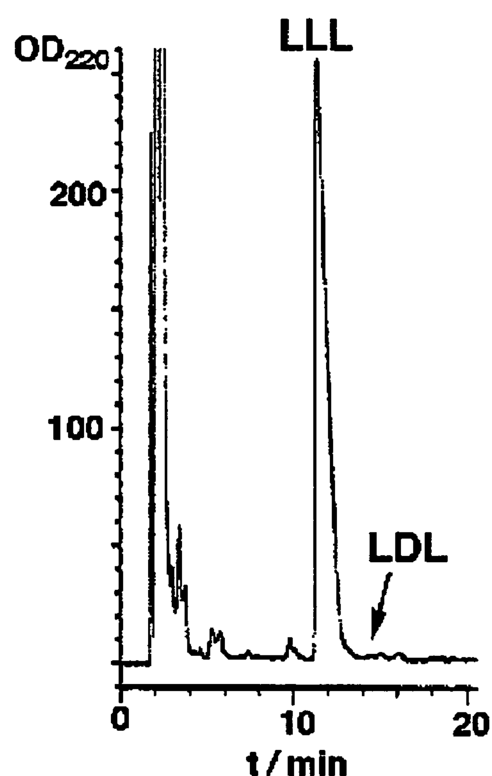
FIG. 3A-3B show HPLC traces of the crude products of oxidation and cleavage.
Figure 3B:
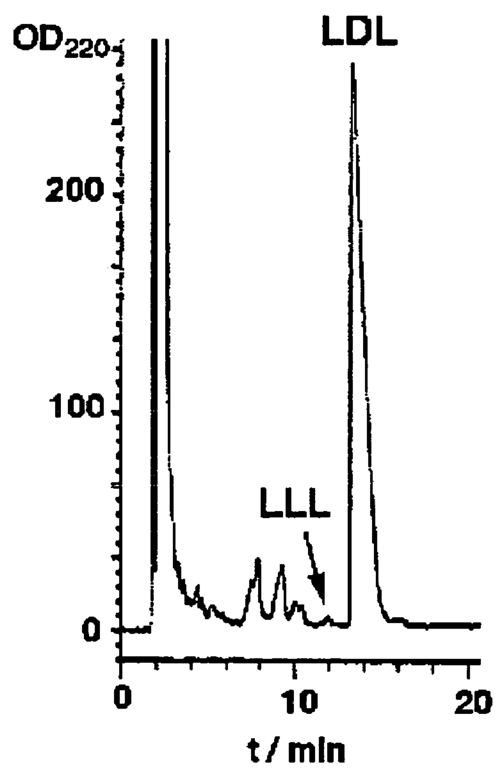

Epimerization of the C-terminal residue attached to the acyl-diazene resin through oxazolone formation was investigated. (See Benoiton, N. L. *Biopolymers* 1996, 40, 245.) Two dipeptide diastereomers (LL- and LD-Phe-Ala peptides) were assembled on the hydrazine resin, oxidized with NBS and then reacted with H-(L)-Ala-OMe. FIGS. 3A and 3B show epimerization studies of the C-terminal residue attached to the resin during the activation of the hydrazide linker with NBS. The HPLC of the crude products from the oxidation of H-(L)-Phe-(L)-Ala-hydrazide resin with NBS and subsequent cleavage by H-(L)-Ala-OMe is shown in FIG. 3A. The HPLC traces of the crude products for the oxidation of (L)-Phe-(D)-Ala-hydrazide resin with NBS and cleavage with H-(L)-Ala-OMe is shown in FIG. 3B. HPLC analysis of the crude cleavage reactions for both tripeptides did not reveal significant epimerization of the penultimate residue (less than 0.5%). These results are in good agreement with previous studies where the hydrazine linker has been oxidatively cleaved and no or little racemization was observed. (See Wolman, Y.; Gallop, P. M.; Patchomik, A. *J. Am. Chem. Soc.* 1961, 83, 1263, Milne, H. B.; Most, C. F. *J. Org. Chem.* 1968, 33, 169, Rosenbaum, C.; Waldmann, H. *Tetrahedron Lett.* 2001, 42, 5677.)

Stability of the Peptide-Resin to the Oxidation Step

TABLE 2

| Peptide | Sequence | Mw/Da | | Yield %[a] | Protecting group |
|---|---|---|---|---|---|
| SEQ ID NO: 4 | H-L<u>Y</u>KAA-SEt | 608.8[b] | 608.0[c] | 90 | Tyr(t-Bu) |
| SEQ ID NO: 5 | H-L<u>W</u>AG-SEt | 489.6[b] | 490.0[c] | 80 | Trp(Boc) |
| SEQ ID NO: 6 | H-L<u>M</u>YKAG-SEt | 726.0[b] | 725.0[c] | 85 | None |
| SEQ ID NO: 7 | H-L<u>C</u>YKAA-SEt | 712.0[b] | 712.1[c] | 70 | Cys(Trt) |
| SEQ ID NO: 8 | H-<u>C</u>YAVTGKDSPAAG-SEt | 1494.7[b] | 1494.5[c] | 75 | Cys(Npys) |

TABLE 2-continued

| Peptide | Sequence | Mw/Da | | Yield %[a] | Protecting group |
|---|---|---|---|---|---|
| SEQ ID NO: 9 | Ac-AEYVRALFDFNGNDEE DLPFKKG-SEt | 2761.1[b] | 2762.2[c] | 35 | (Fmoc-2-hydroxy-4-methylbenzyl)-Gly |

[a]Based on HPLC purity;
[b]theoretical;
[c]actual

Figure 4A:
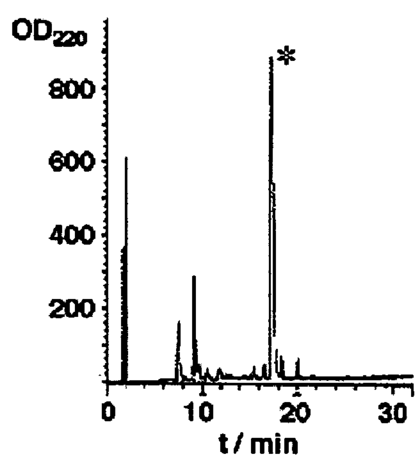
FIGS. 4A-4F show HPLC analysis of the crude products obtained by oxidative cleavage with NBS/H-AA-SEt of peptide SEQ ID NOs: 4-9.
Figure 4D:
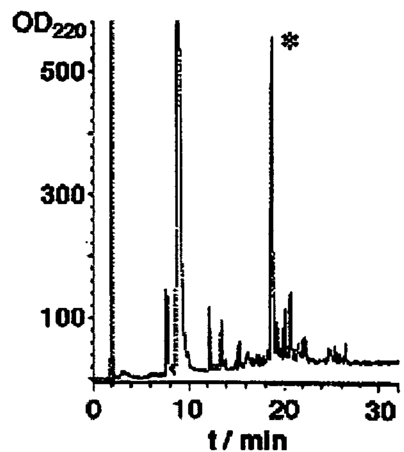
Figure 4B:
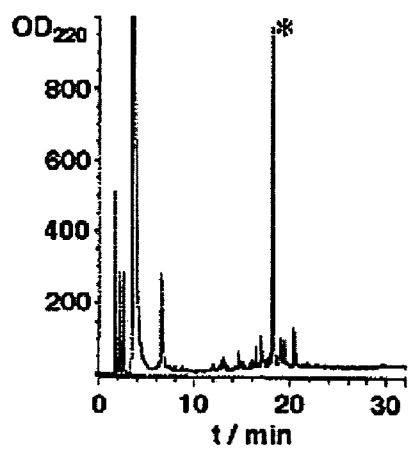
Figure 4E:
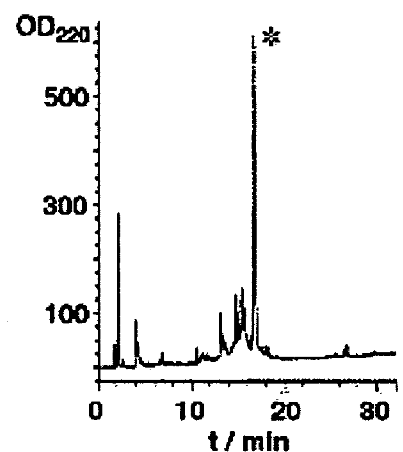
Figure 4C:
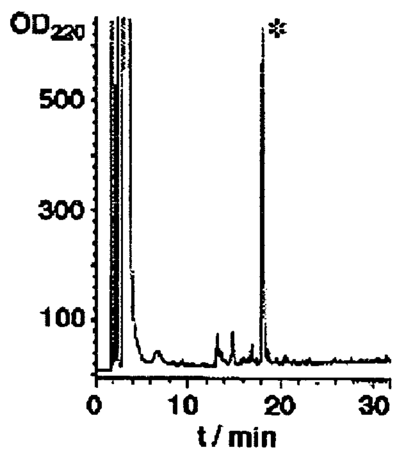
Figure 4F:
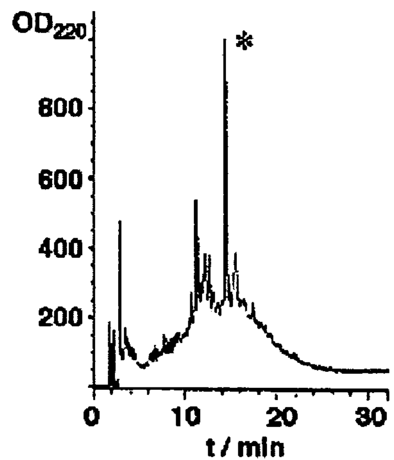

The stability of peptides containing oxidative-sensitive residues (i.e. Tyr, Trp, Met and Cys) during the oxidation step was tested. Referring to Table 2, several peptides containing these residues were synthesized on a hydrazine resin, oxidized with NBS and cleaved with either H-Ala-SEt or H-Gly-SEt. Table 2 shows primary amino acid sequences of peptide thioesters SEQ ID NO: 4 through SEQ ID NO: 9 prepared in this study. The protecting groups for sensitive amino acids (i.e., the underlined residues within the corresponding sequence) are indicated along with the molecular weights for the expected products. The yield data is based on HPLC purity. The protecting groups listed are for the side-chain of peptides SEQ ID NO: 4 through SEQ ID NO: 8 and for the backbone of peptide SEQ ID NO: 9. FIGS. 4A-4F show HPLC analysis of the crude product obtained by oxidative cleavage with NBS/H-AA-SEt of different peptides varying in length and composition. In each case the asterisk denotes the thioester product. A linear gradient of 0-70% buffer B over 30 minutes was used in each case, except in FIG. 4F where a linear gradient of 30-60% buffer B was used. FIGS. 4A-4F correspond to the peptide sequences as follows: FIG. 4A—SEQ ID NO: 4 (a Tyr(t-Bu)-containing peptide); FIG. 4B—SEQ ID NO: 5 (a Trp(Boc)-containing peptide); FIG. 4C—SEQ ID NO: 6 (a Met-containing peptide); FIG. 4D—SEQ ID NO: 7 (a Cys(Trt)-containing peptide); FIG. 4E—SEQ ID NO: 8 (a Cys(Npys)-containing peptide); FIG. 4F—SEQ ID NO: 9 (a Fmoc-2-hydroxy-4 methyl benzyl)-Gly containing peptide); The results, summarized in FIGS. 4A-4F, show that peptides SEQ ID NO: 4 and SEQ ID NO: 5 which contain Tyr(t-Bu) and Trp(Boc) residues, respectively, were not affected during the NBS treatment under the conditions used in this study. In both cases, the major product was the expected peptide α-thioester (as shown by the asterisk in FIGS. 4A and 4B) and minor amounts of by-products. This was significant since phenolic and indole rings are well known to be very susceptible to halogenation by mildly oxidizing agents such as NBS. (See Verza, G.; Bakas, L. Biochim. Biophys. Acta 2000, 1464, 27.) In the case of the Tyr residue, the t-butyl side chain protecting group prevented any detectable bromination of the aromatic ring under the conditions employed. This may be due to a combination of the steric effect of the t-butyl group on the positions 3 and 5 of the phenolic ring and the kinetic control conditions used during the oxidation step (i.e., short reaction times and use of slight excess of oxidizing agent). The alternative use of electron withdrawing groups has been also reported to protect the phenolic group of Tyr from oxidative halogenation. (See Powers, S. P.; Pinon, D. I.; Miller, L. J. Int. J. Pept. Prot. Res. 1988, 31, 429.) More striking, however, is the fact that Trp totally resisted oxidation under the reaction conditions shown in FIG. 1 when protected with the $N^{in}$-Boc group. In contrast, when peptide SEQ ID NO: 5 was synthesized without protection on the indole ring, the oxidation and cleavage with NBS and H-Gly-SEt gave a complex reaction mixture where different oxidation/bromination products could be easily identified by HPLC and ESMS. The protective effect of the $N^{in}$-Boc group may arise from the electron withdrawing character of the carbamate moiety which leads to the partial deactivation of the indole ring towards electrophiles. (See Noda, M.; Kiffe, M. *J. Pept. Res.* 1997, 50, 329.)

Referring to FIG. 4C, Met-containing peptide SEQ ID NO: 6 was completely oxidized to the corresponding sulfoxide during the NBS oxidation step, but during the subsequent TFA deprotection step, the sulfoxide was reduced when the reaction was carried out for 3 h at room temperature in the presence of 2% EtSH.

Referring to FIG. 4D, Cys(Trt)-containing peptide SEQ ID NO: 7 was also oxidized during the NBS treatment showing a rather complex crude mixture after the TFA deprotection step. However, as shown in FIG. 4D, the desired thioester peptide SEQ ID NO: 7 could be obtained in good yield if the crude TFA cleavage product was reduced with EtSH at pH 8.0 for 30 minutes. Under these conditions the hydrolysis of the α-thioester was minimal. Oxidation of the Cys residue during the activation step, however, could be totally avoided if the thiol group of the Cys residue was protected as a mixed disulfide. Aryl and alkyl mixed disulfides are known to be stable to mild oxidation conditions. (See Andreu, D.; Albericio, F.; Sole, N. A.; Munson, M. C.; Ferrer, M.; Barany, G. In Methods in Molecular Biology: Peptide Synthesis Protocols; Pennington, M. W., Dunn, B. M., Eds.; Humana Press Inc.: Totowa, N.J., 1994; Vol. 35, pp 91-169.)

Referring to FIG. 4E, Cys-containing peptide SEQ ID NO: 8, where the N-terminal Cys residue was introduced as Boc-Cys(Npys), remained totally stable during the oxidation of the hydrazine linker and reduction was not required to obtain the corresponding thioester peptide in good yield. (See Bernatowicz, M. S.; Matsueda, R.; Matsueda, G. R. *Int. J. Pept. Prot. Res.* 1986, 28, 107). The Npys protecting group can only be used in those peptides where the Cys residue is at the N-terminal position due to its partial lability to the conditions employed in the Fmoc deprotection step. Thus, in peptides where the Cys residue is not located in this position, the S-StBu group should be used. (See Ludolph, B.; Waldmann, H. *Chem. Eur. J.* 2003, 9, 3683.) The S-StBu group is totally compatible with Boc- and Fmoc-strategies and can easily be deprotected by reductive treatment with thiols or phosphines. (See Eritja, R.; Ziehler-Martin, J. P.; Walker, P. A.; Lee, T. D.; Legesse, K.; Albericio, F.; Kaplan, B. E. *Tetrahedron* 1987, 43, 2675.)

Finally, the oxidative-cleavage procedure depicted in FIG. 1 was also used to generate a more complex and larger peptide thioester. Peptide thioester SEQ ID NO: 9, a 22-residue thioester peptide derived from the N-terminal SH3 domain of the c-Crk protein adaptor, was prepared to obtain the full synthetic SH3 domain by native chemical ligation. (See Knudsen, B. S.; Feller, S. M.; Hanafusa, H. *J. Biol. Chem.* 1994, 269, 32781.) Referring to FIG. 4F, crude peptide (See Ludolph, B.; Waldmann, H. Chem. Eur. J. 2003, 9, 3683.) α-thioester SEQ ID NO: 9 was relatively clean showing only two major peaks by HPLC. The major peak corresponded to the expected peptide thioester SEQ ID NO: 9 as determined by mass spectrometry. The secondary peak (ca. 33% of the first peak) which eluted earlier in the HPLC chromatography, presented a loss of 17 Da versus peptide SEQ ID NO: 9 and it was assigned to be the aspartimide derivative of peptide SEQ ID NO: 9. Aspartimide formation could be minimized, although not totally avoided, by using the Fmoc-(Fmoc-2-hydroxy-4-methylbenzyl)-Gly derivative at $^{12}$Gly in peptide SEQ ID NO: 9. (See Quibell, M.; Owen, D.; Packman, L. C.; Johnson, T. *J. Chem. Soc., Chem. Commun.* 1994, 2343; Offer, J.; Quibell, M.; Johnson, T. *J. Chem. Soc., Perkin Trans.* 1 1996, 175.)

After a single HPLC purification step, pure peptide SEQ ID NO: 9 was obtained with a modest yield (ca. 25%). However, the synthesis of this fragment by itself was particularly challenging due to the presence of the Asn-Gly sequence, which is prone to form the corresponding aspartimide.

Native Chemical Ligation

In order to test the suitability of the thioesters generated by the method disclosed herein, peptides SEQ ID NO: 8 and SEQ ID NO: 9 were used for carrying out intramolecular and intermolecular native chemical ligations.

Figure 5A:
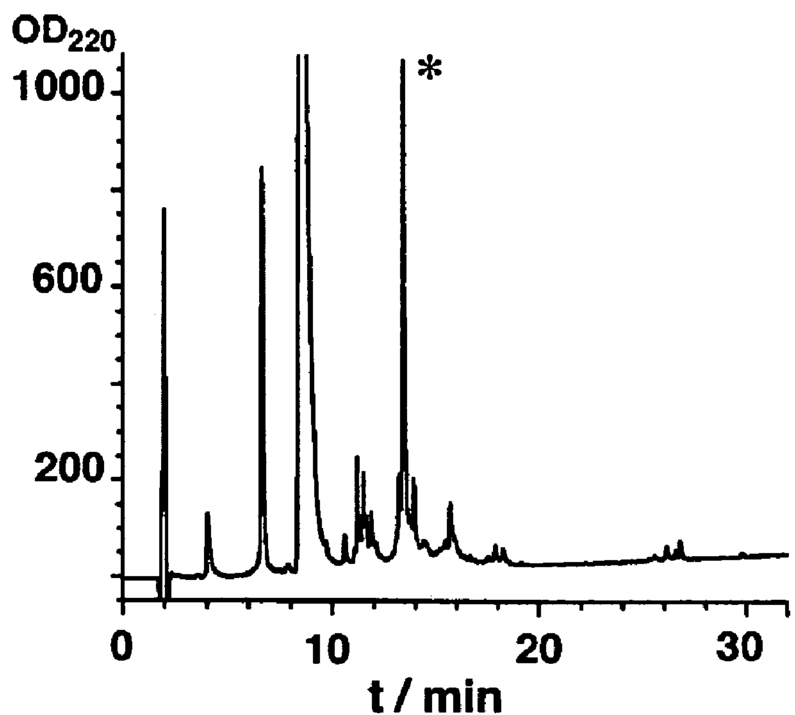
FIG. 5A shows HPLC analysis of the crude cyclization mixture of peptide SEQ ID NO: 8.
Figure 5B:
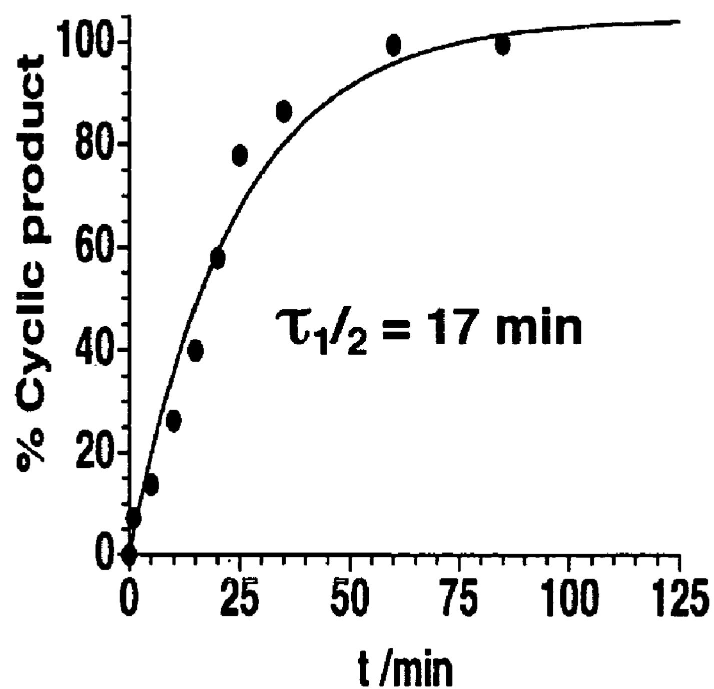
FIG. 5B shows kinetics for the cyclization of linear precursor peptide SEQ ID NO: 8.

Intramolecular Native Chemical Ligation. Linear precursor peptide SEQ ID NO: 8, with a sequence deriving from the tenth type 3 module of Fibronectin (a natural β-strand hairpin), was designed to contain an α-thioester group and a Cys residue at the C- and N-terminal positions, respectively. (See Pierschbacher, M. D.; Ruoslahti, E. *Nature* 1984, 309, 30.) The presence of these two chemical moieties allows the backbone cyclization by intramolecular native chemical ligation. Cyclization of peptide SEQ ID NO: 8 was accomplished by diluting the crude TFA cleavage material in freshly degassed 0.2 M sodium phosphate buffer at pH 7.2 containing 2% EtSH to a final concentration of ca. 200 μM. Under these conditions the backbone cyclization reaction proceeded quickly and efficiently. The reaction was complete in less than 60 min and the major product corresponded to cyclic peptide SEQ ID NO: 8 as characterized by ES-MS and tryptic digestion. FIG. 5A is an HPLC analysis of the crude cyclization mixture after 1 hour. The cyclic product is marked with an asterisk. HPLC analysis was carried out using a linear gradient of 0-70% buffer B over 30 minutes. FIG. 5B shows the kinetics for the cyclization of linear precursor peptide SEQ ID NO: 8.

Intermolecular Native Chemical Ligation-Synthesis of functional SH3 protein domain. The N-terminal SH3 domain from the c-Crk adaptor protein was used as a synthetic target employing intermolecular native chemical ligation. (See Knudsen, B. S.; Feller, S. M.; Hanafusa, H. *J. Biol. Chem.* 1994, 269, 32781.) The amino acid sequence of the c-Crk N-terminal SH3 protein domain corresponds to residues 134-190 of the c-Crk protein. Retrosynthetic analysis, guided by the structure of the SH3 domain (See Wu, X.; Knudsen, B.; Feller, S. M.; Zheng, J.; Sali, A.; Cowburn, D.; Hanafusa, H.; Kuriyan, J. *Structure* 1995, 3, 215.) suggested that a functional analogue of the protein domain could be prepared by native chemical ligation between peptide SEQ ID NO: 9 (residues 134-156, Table 2) and peptide SEQ ID NO: 10 (residues 157-191, CILRIRDKPEEQWWNAEDSEGKRG-MIPVPYVEKYG). Peptide SEQ ID NO: 10 was synthesized using a Fmoc-protocol on a Rink-amide resin. In order to facilitate ligation, a Cys residue was introduced at the N-terminus of peptide SEQ ID NO: 10.

The ligation reaction between peptide SEQ ID NO: 9 and peptide SEQ ID NO: 10 was performed by mixing equimolar amounts of both peptides in 0.2 M sodium phosphate at pH 7.2 containing 2% EtSH. FIG. 6A is an HPLC analysis of the intermolecular ligation crude mixture after 36 hours. The ligated product is marked with an asterisk. Referring to FIG. 6A, the reaction was shown to be complete in 36 h, as indicated by HPLC analysis. The ligation product was by far the main product and could be easily isolated by semipreparative HPLC. Referring to FIG. 6B, characterization of the product by ES-MS confirmed the identity of the SH3 ligated domain. The ligated SH3 domain was readily purified by HPLC and refolded by flash dilution in 20 mM sodium phosphate, 100 mM NaCl at pH 7.2. The ligand binding activity of the synthetic SH3 domain was evaluated using a fluorescence-based titration assay. (See Camarero, J. A.; Ayers, B.; Muir, T. W. *Biochemistry* 1998, 37, 7487.) FIG. 6C shows the change in fluorescence emission intensity of the ligated SH3 domain upon addition of proline-rich ligand peptide SEQ ID No: 11 (L). Referring to FIG. 6C, the equilibrium dissociation constant for binding of the synthetic SH3 domain to the natural proline-rich peptide ligand C3G i.e., PPPALPPKKR (peptide SEQ ID NO: 11), was 0.9 μM. (See Knudsen, B. S.; Feller, S. M.; Hanafusa, H. *J. Biol. Chem.* 1994, 269, 32781.) This value is identical to that reported for the recombinant c-Crk N-terminal SH3 domain. (See Camarero, J. A.; Fushman, D.; Sato, S.; Giriat, I.; Cowburn, D.; Raleigh, D. P.; Muir, T. W. *J Mol Biol* 2001, 308, 1045.)

EXPERIMENTAL

Glycine S-Ethyl Ester, Hydrochloride Salt (H-Gly-SEt-.HCl). Boc-Gly-OH (5.0 g, 28.5 mmol) and 1-hydroxybenzotriazole hydrate (HOBt.$H_2O$; 4.36 g, 28.5 mmol) were dissolved in DCM (125 mL). 1-(3-dimethylaminopropyl)-3-ehylcarbodiimide (EDC, 4.95 mL, 28.5 mmol) and N,N-diisopropylethylamine (DIEA; 5 mL, 28.5 mmol) were added sequentially to the reaction mixture, and the resulting reaction was allowed to stir for 90 min. At this point, ethylthiol (5 mL, 67.5 mmol) was added in one portion and the homogeneous reaction was kept for 4 h at room temperature. The crude reaction mixture was then washed with 1 M aqueous HCl (3×250 mL), 1% $NaHCO_3$ (3×250 mL) and $H_2O$ (3×250 mL), dried over $MgSO_4$ and concentrated in vacuo. The resulting residue (Boc-Gly-SEt) was dissolved in 4 M HCl-dioxane (20 mL) and stirred at room temperature for 90 min. The homogeneous reaction solution was concentrated in vacuo and the product was precipitated with cold anhydrous $Et_2O$ (50 mL). The precipitate was filtered and dried under vacuum to provide the title product as a white solid (2.1 g, 60%) >99.5% pure glycine ethyl thioester by analytical RP-HPLC ($t_R$: 3.49 min using an isochratic of 0% B for 2 min and then a linear gradient of 0% to 17% B over 10 min): $^1$H NMR (DMSO-$d_6$) δ 8.32 (br, s, 3H), 4.05 (s, 2H), 2.95 (q, 2H), 1.19 (t, 3H); ESMS: calculated for $C_4H_9NOS$ (average isotope composition) 119.2 Da, found 119.0±0.5 Da.

Solid-Phase Peptide Synthesis. All peptides were manually synthesized using the HBTU activation protocol for Fmoc solid-phase peptide synthesis on a Rink-amide resin (peptide SEQ ID NO: 10 and SEQ ID NO:11) or on a 4-Fmoc-hydrazinobenzoyl AM resin (peptides SEQ ID NO: 1 to SEQ ID NO: 9). (See Fields, G. B.; Noble, R. L. *Int. J. Peptide Protein Res.* 1990, 35, 161.)

Coupling yields were monitored by the quantitative ninhydrin determination of residual free amine. (See Sarin, V. K.; Kent, S. B. H.; Tam, J. P.; Merrifield, R. B. *Anal. Biochem.* 1981, 117, 147) Side-chain protection was employed as previously described for the Fmoc-protocol except for peptides SEQ ID NO: 5, SEQ ID NO: 6, SEQ ID NO: 8, and SEQ ID NO: 9 where Fmoc-Trp(Boc)-OH, unprotected Fmoc-Met-OH, Boc-Cys(Npys)-OH and Fmoc-(Fmoc-2-hydroxy-4-methylbenzyl)-Gly-OH (at $^{12}$Gly in peptide SEQ ID NO: 9 to minimize aspartimide formation) were used respectively.

Oxidation and Cleavage of the Hydrazine Linker. The corresponding peptide-hydrazide resin (50 mg, ≈20-30 μmol depending on resin substitution) was swollen in anhydrous DCM for 20 min and drained. N-Bromosuccinimide (NBS; 13 mg, 75 μmol) and anhydrous pyridine (25 μL, 310 μmol) were dissolved in anhydrous DCM (5 mL) and then added to the peptide-resin. The oxidation reaction was kept for 10 min at room temperature with occasional stirring. Unreacted NBS was removed by washing the peptide-resin with anhydrous DCM (3×5 mL). Either H-Gly-SEt.HCl (50 mg, 322 μmol) or H-Ala-SEt.HCl (54 mg, 320 μmol) and DIEA (200 μL, 1.1 mmol) were dissolved in DCM (5 mL), and the solution was immediately added to the oxidized peptide resin. The cleavage reaction was kept for 1 h at room temperature. The reaction was then quenched with HOAc (250 μL) and the solvent was removed in vacuo. The peptide thioester was deprotected when necessary with TFA:$H_2O$:trisisopropylsilane (TIS; 50:1:1 v/v, 5 mL) for 1-3 h, except in peptide 6 where TIS was replaced by EtSH as scavenger in the deprotection cocktail. The filtrate from the cleavage reaction was combined with TFA washes (2×0.5 mL) from the cleaved peptide resin and concentrated under a stream of $N_2$. Precipitation with cold anhydrous $Et_2O$ (50 mL) afforded crude product which was washed with $Et_2O$ (2×20 mL). The crude peptide was dissolved in buffer A:buffer B (4:1 vol, 5 mL) and characterized by HPLC and ESMS and further purified by either semi- or preparative HPLC.

Synthesis of Ac-IAFG-SEt (1). The synthesis (0.1 mmol) was carried out on a 4-Fmoc-hydrazinobenzoyl AM resin (0.98 mmol/g) as described above. When the assembly was complete, the Fmoc-$N^{\alpha}$ protecting group was removed by treatment with 1% DBU and 20% piperidine solution in DMF (5+10 min) and then acetylated with $Ac_2O$/DIEA/DMF (15:15:70) for 10 min. The oxidation with NBS and cleavage with H-Gly-SEt.HCl was carried out as described above. The major product was characterized as the desired thioester product by ESMS: calculated for $C_{24}H_{36}N_4O_5S$ (average isotope composition) 492.6 Da, found 492.0±0.5 Da.

Kinetics Studies of the Cleavage of Peptide 3. Kinetic analyses were performed by analytical HPLC. The oxidation and cleavage for obtaining peptide thioester SEQ ID NO: 3 were performed as described above. Small aliquots of supernatant (20 μL) were withdrawn from the cleavage reaction with H-Gly-SEt at various times, treated with 100 μL of TFA for 20 min and then evaporated under a stream of $N_2$. The peptide thioester was solubilized with buffer A:buffer B (2:1 vol., 150 μL), filtered and analyzed by HPLC. The half life was calculated by measuring the concentrations of the thioester peptide and fitting the time course data to the equation: $C_{t,thioester}=C_{0.thioester}\cdot(1-e^{-kt})$, where $C_{t,thioester}$ is the concentration of thioester peptide time t, $C_{0.thioester}$ is the final concentration of thioester peptide and k the rate constant.

Epimerization studies. The synthesis (0.1 mmol) of (L)-Phe-(L)-Ala and (L)-Phe-(D)-Ala peptide diastereomers and oxidation with NBS was carried out as described as above with the exception that H-(L)-Ala-OMe.HCl (45 mg, 322 μmol) was used to trap the peptidyl diazene intermediate. The TFA deprotection step was carried out for 1 h as described and the major product in each case was characterized as the desired tripeptide methyl ester by ESMS: calculated for $C_{16}H_{23}N_3$ (average isotope composition) 321.4 Da, found 321.0±1.0 Da. The two peptide diastereomers were resolved by analytical HPLC using a linear gradient of 10-15% B over 30 min ($t_R$ for LLL and LDL peptides was 12.3 min and 13.6 min respectively).

Cyclization of H-C(Npys)YAVTGKGDSPAAG-SEt (SEQ ID NO: 8). The crude peptide SEQ ID NO: 8 (5 mL, ca. 5 μmol) was diluted with 0.2 M sodium phosphate buffer at pH 7.5 (20 mL) to a final concentration≈200 μM. The final pH was adjusted to 7.2 when necessary with concentrated aqueous NaOH solution and then the reaction was initiated by adding EtSH (200 μL). The cyclization reaction was allowed to proceed for 1 h at room temperature. The major peptide product was then purified by semipreparative HPLC using a linear gradient of 0-50% B over 30 min. The purified product was characterized as the cyclomonomeric product by tryptic digestion and ESMS: calculated for $C_{54}H_{84}N_{16}O_{18}S$ (average isotope composition) 1278.4 Da, found 1278.0±0.1 Da.

Kinetic Studies on Cyclization of Peptide (SEQ ID NO: 8). Kinetic analyses were performed by analytical HPLC. The reactions were initiated as described above. Aliquots of the supernatant (50 μL) were withdrawn at various time points, treated with 10 μL of a 50 mM dithiotreitol (DTT) solution and analyzed by HPLC. The first order rate constant and the half life were calculated by measuring the concentrations of the cyclic peptide and fitting the time course data to the equation: $C_{t.cyclic}=C_{0.cyclic}\cdot(1-e^{-kt})$, where $C_{t.cyclic}$ is the concentration of cyclic peptide at time t, $C_{0.cyclic}$ is the final concentration of cyclic peptide and k the rate constant.

Synthesis of c-Crk SH3 Domain by Native Chemical Ligation (Ligation of Peptides SEQ ID NO: 9 and SEQ ID NO: 10). Peptide thioester SEQ ID NO: 9 (1.9 mg, 0.69 μmol) and peptide SEQ ID NO: 10 (3.1 mg, 0.74 μmol) were dissolved in 0.2 M sodium phosphate buffer at pH 7.2 containing 5% EtSH by volume. The ligation was allowed to proceed for 72 h at room temperature. The reaction was then quenched with an excess of DTT and the ligated product purified by semipreparative HPLC using a linear gradient of 20-55% B over 30 min (2.2 mg, 46%). The purified product was characterized as the ligated SH3 domain by ESMS: calculated for $C_{310}H_{464}N_{82}O_{93}S_2$ (average isotope composition) 6891.7 Da, found 6894.1±1.0 Da.

Fluorescence-based Ligand Binding Assay. The equilibrium dissociation binding constant of synthetic SH3 domain for ligand SEQ ID NO: 11 was obtained using a fluorescence-based titration assay. Measurements were conducted at 25° C. in a stirred 1 cm-pathlength cell using a Fluorolog III instrument. Excitation was at 300 nm with a 2.5 nm slit and the fluorescence emission was monitored at 348 nm through a 5 nm slit. The protein concentration was 0.5 μM in a buffer containing 20 mM sodium phosphate, 100 mM NaCl at pH 7.2. The dissociation constant was determined by changes in the fluorescence of the protein solution upon addition of the corresponding peptide ligand at defined concentrations; calculations were made assuming formation of a 1:1 complex. (See Camarero, J. A.; Ayers, B.; Muir, T. W. *Biochemistry* 1998, 37, 7487.)

A new method for the facile preparation of peptide thioesters without limitations of size and amino acid composition has been developed and is disclosed herein. The oxidation and cleavage reactions have been shown to be totally compatible with sensitive amino acids when the appropriate protecting groups and oxidative conditions are employed. No detectable racemization was observed during the activation and cleavage of the hydrazide linker. The synthetic method disclosed herein does not require special linkers, resins or complicated protocols as commercially available hydrazine resins are employed and the assembly of the peptide chain is carried out using standard SPPS methods.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in organic chemistry, biochemistry or related fields are intended to be within the scope of the following claims.

The invention claimed is:

1. A method of cleaving a peptide from solid phase comprising: providing a protected peptide linked to a solid phase having a hydrazide linker; oxidizing said hydrazide linker with an oxidizer to form a solid phase peptide having an acyl diazene functional group or moiety, wherein said oxidizer and said solid phase peptide are present in a ratio, and cleaving said acyl diazene functional group or moiety with a cleaving agent, wherein said cleaving agent is an alpha amino acid thioester.

2. The method recited in claim 1, wherein said oxidizer comprises N-bromosuccinimide.

3. The method recited in claim 2, wherein the ratio of oxidizer to peptide ranges from 1 to 2 equivalents.

4. The method recited in claim 2, wherein the oxidation is allowed to occur for no longer than 10 minutes.

5. The method recited in claim 1, wherein the cleavage of said acyl diazene derivative is accomplished by using at least 10 equivalents of alpha amino acid thioester.

6. The method recited in claim 1, wherein the solid phase peptide is protected using protecting groups compatible with Fmoc-based solid phase peptide synthesis.

7. The method recited in claim 6, further comprising: removing the protecting groups by acidolytic treatment with trifluoroacetic acid after said cleaving step is performed.

8. A method of cleaving a peptide from solid phase comprising: providing a solid phase linked peptide having a hydrazide linker; oxidizing said hydrazide linker with an oxidizer to form a solid phase peptide having an acyl diazene functional group or moiety; and cleaving said acyl diazene functional group or moiety with a cleaving agent, wherein said cleaving agent is a thiol.

9. A method of cleaving a peptide from solid phase comprising: providing a solid phase linked peptide having a hydrazide linker: oxidizing said hydrazide linker with an oxidizer to form a solid phase peptide having an acyl diazene functional group or moiety; and cleaving said acyl diazene functional group or moiety with a cleaving agent, wherein said cleaving agent is an S-nucleophile.

10. The method of claim 1, wherein said thioester is an alpha amino acid S-alkyl thioester.

11. The method of claim 1, wherein an alpha amino group of said peptide is protected by a protecting group.

12. The method of claim 11, wherein said protecting group is a BOC-$^{\alpha}$N-derivative.

13. The method of claim 1, wherein said peptide comprises a C-terminal amino acid selected from the group consisting of Gly and Ala.

14. The method of claim 6, wherein said protecting groups are selected from the group consisting of: t-Bu, Boc, trityl (Trt), nitro-2-pyridinesulfenyl (Npys), and Fmoc-2-hydroxy-4-methylbenzyl.

15. The method of claim 7, further comprising:

producing a peptide alpha-thioester after said removing step is performed.

16. The method of claim 14, wherein said protecting group is t-Bu.

* * * * *

SEQUENCE LISTING

```
<160> NUMBER OF SEQ ID NOS: 11

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Ile Ala Phe Gly
  1


<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Ile Ala Phe Ala
  1


<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Leu Phe Ala Gly
  1


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Leu Tyr Lys Ala Ala
  1               5


<210> SEQ ID NO 5
```

-continued

```
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Leu Trp Ala Gly
  1


<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Leu Met Tyr Lys Ala Gly
  1               5


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Leu Cys Tyr Lys Ala Ala
  1               5


<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Cys Tyr Ala Val Thr Gly Lys Asp Ser Pro Ala Ala Gly
  1               5                  10


<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Ala Glu Tyr Val Arg Ala Leu Phe Asp Phe Asn Gly Asn Asp Glu Glu
  1               5                  10                  15

Asp Leu Pro Phe Lys Lys Gly
             20


<210> SEQ ID NO 10
<211> LENGTH: 35
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 10

Cys Ile Leu Arg Ile Arg Asp Lys Pro Glu Glu Gln Trp Trp Asn Ala
  1               5                  10                  15

Glu Asp Ser Glu Gly Lys Arg Gly Met Ile Pro Val Pro Tyr Val Glu
             20                  25                  30

Lys Tyr Gly
         35


<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Pro Pro Pro Ala Leu Pro Pro Lys Lys Arg
  1               5                  10
```